(12) United States Patent
Shekalim et al.

(10) Patent No.: US 11,382,521 B2
(45) Date of Patent: Jul. 12, 2022

(54) GUIDEWIRE SYSTEM FOR INTRA-VASCULAR PRESSURE MEASUREMENT

(71) Applicant: CARDIOSERT LTD., Nesher (IL)

(72) Inventors: Avraham Shekalim, Nesher (IL); Noam Peleg, Gan Ner (IL)

(73) Assignee: CARDIOSERT LTD., Nesher (IL)

( * ) Notice: Subject to any disclaimer, the term of this patent is extended or adjusted under 35 U.S.C. 154(b) by 313 days.

(21) Appl. No.: 16/466,644

(22) PCT Filed: Dec. 5, 2017

(86) PCT No.: PCT/IL2017/051320
§ 371 (c)(1),
(2) Date: Jun. 5, 2019

(87) PCT Pub. No.: WO2018/104941
PCT Pub. Date: Jun. 14, 2018

(65) Prior Publication Data
US 2019/0343404 A1    Nov. 14, 2019

Related U.S. Application Data

(60) Provisional application No. 62/429,902, filed on Dec. 5, 2016.

(51) Int. Cl.
*A61B 5/0215* (2006.01)
*A61B 5/00* (2006.01)
*G01L 19/00* (2006.01)

(52) U.S. Cl.
CPC .......... *A61B 5/0215* (2013.01); *A61B 5/6851* (2013.01); *A61B 2562/0247* (2013.01)

(58) Field of Classification Search
CPC ................ A61B 5/0215; A61B 5/6851; A61B 2562/0247; G01L 19/0007
See application file for complete search history.

(56) References Cited

U.S. PATENT DOCUMENTS

| | | | | |
|---|---|---|---|---|
| 5,308,324 A * | 5/1994 | Hammerslag | ..... | A61M 25/0144 600/585 |
| 5,964,714 A * | 10/1999 | Lafontaine | ........... | A61B 5/0215 600/561 |
| 6,346,084 B1 * | 2/2002 | Schnell | ................ | A61B 5/0215 600/561 |

(Continued)

*Primary Examiner* — Devin B Henson
*Assistant Examiner* — Justin Xu
(74) *Attorney, Agent, or Firm* — Mark M. Friedman

(57) ABSTRACT

A pressure-measuring guidewire system includes a hollow guidewire (110) in sealed interconnection with a contained volume (102) of a connector (101). The contained volume is bordered on at least one side by a septum (103). A pressure sensor unit (122) includes a transducer (130) associated with a hollow needle (131) which can be inserted to penetrate the septum (103), thereby connecting the transducer with a column of fluid within an inner lumen of the guidewire (102). Priming of the guidewire is performed prior to use, typically by use of a syringe, prior to connection of the sensor unit, thereby protecting the transducer from damage from the priming pressure. Also disclosed is a guidewire tip configuration which provides effective fluid connection for pressure measurement while maintaining the properties of a conventional guidewire.

12 Claims, 14 Drawing Sheets

(56) References Cited

U.S. PATENT DOCUMENTS

| | | | |
|---|---|---|---|
| 2003/0100838 A1* | 5/2003 | Ehr | A61B 5/6851 600/486 |
| 2011/0046477 A1* | 2/2011 | Hulvershorn | A61M 5/46 600/424 |
| 2011/0060229 A1* | 3/2011 | Hulvershorn | A61M 25/06 600/486 |
| 2011/0144531 A1* | 6/2011 | Marcotte | A61F 5/0056 600/561 |
| 2012/0065482 A1* | 3/2012 | Robinson | A61B 5/14557 600/309 |
| 2014/0276142 A1* | 9/2014 | Dorando | A61B 5/02007 600/486 |

* cited by examiner

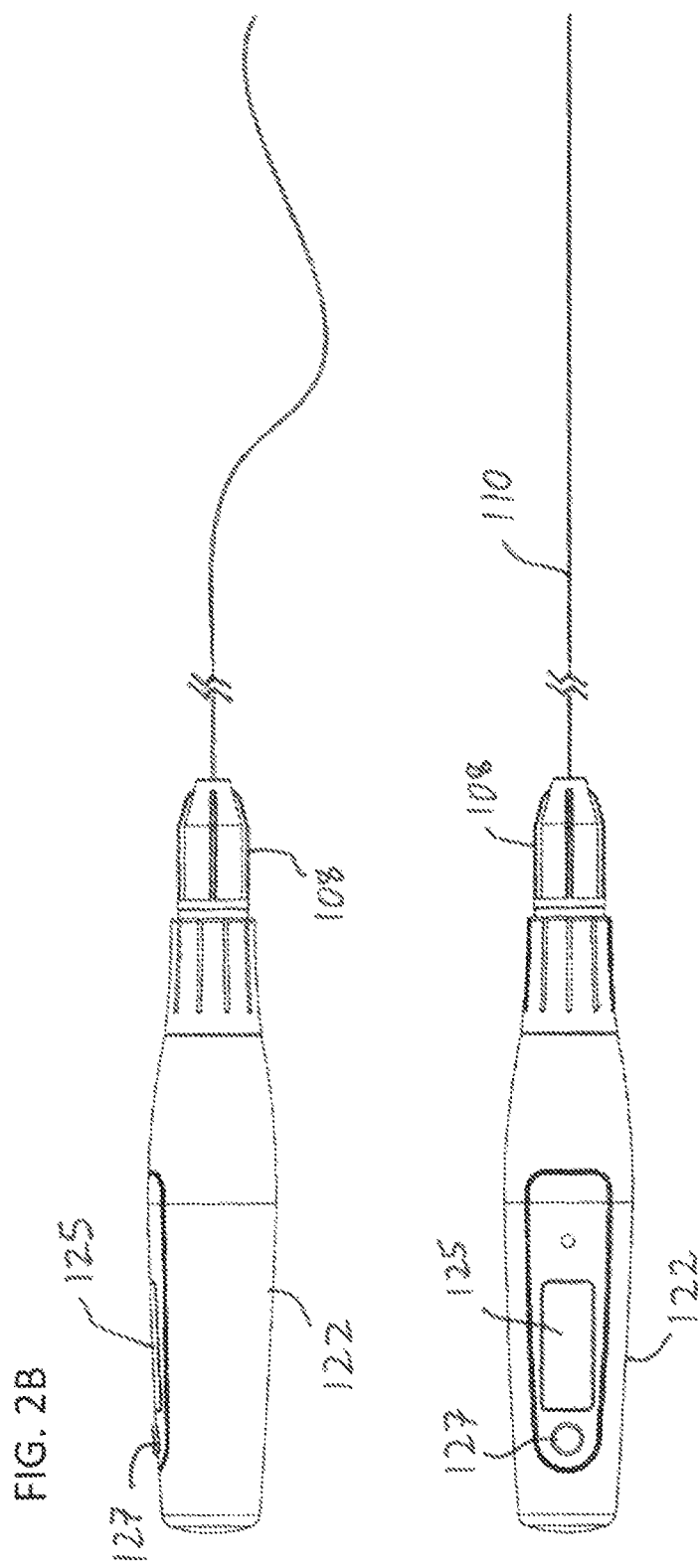

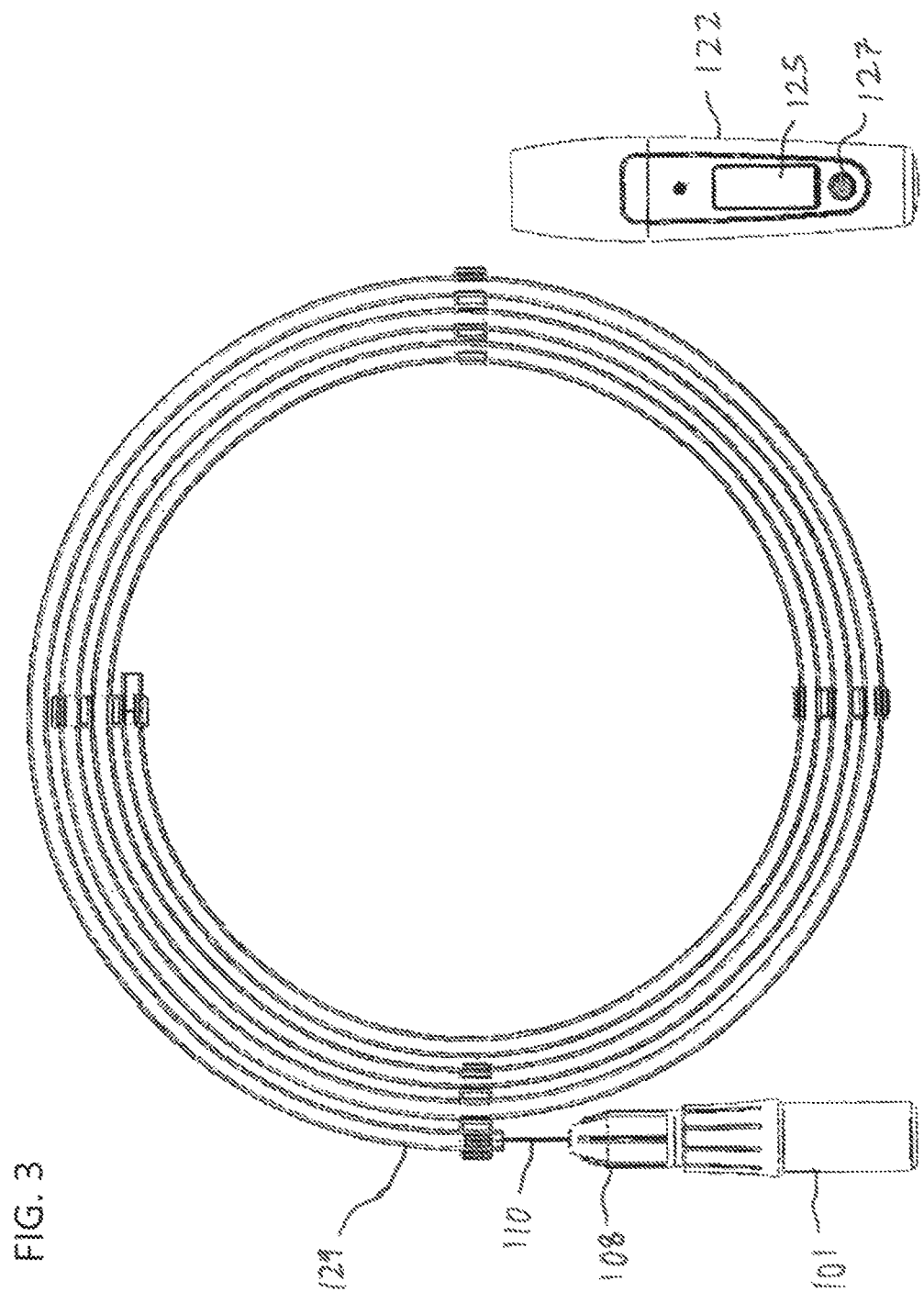

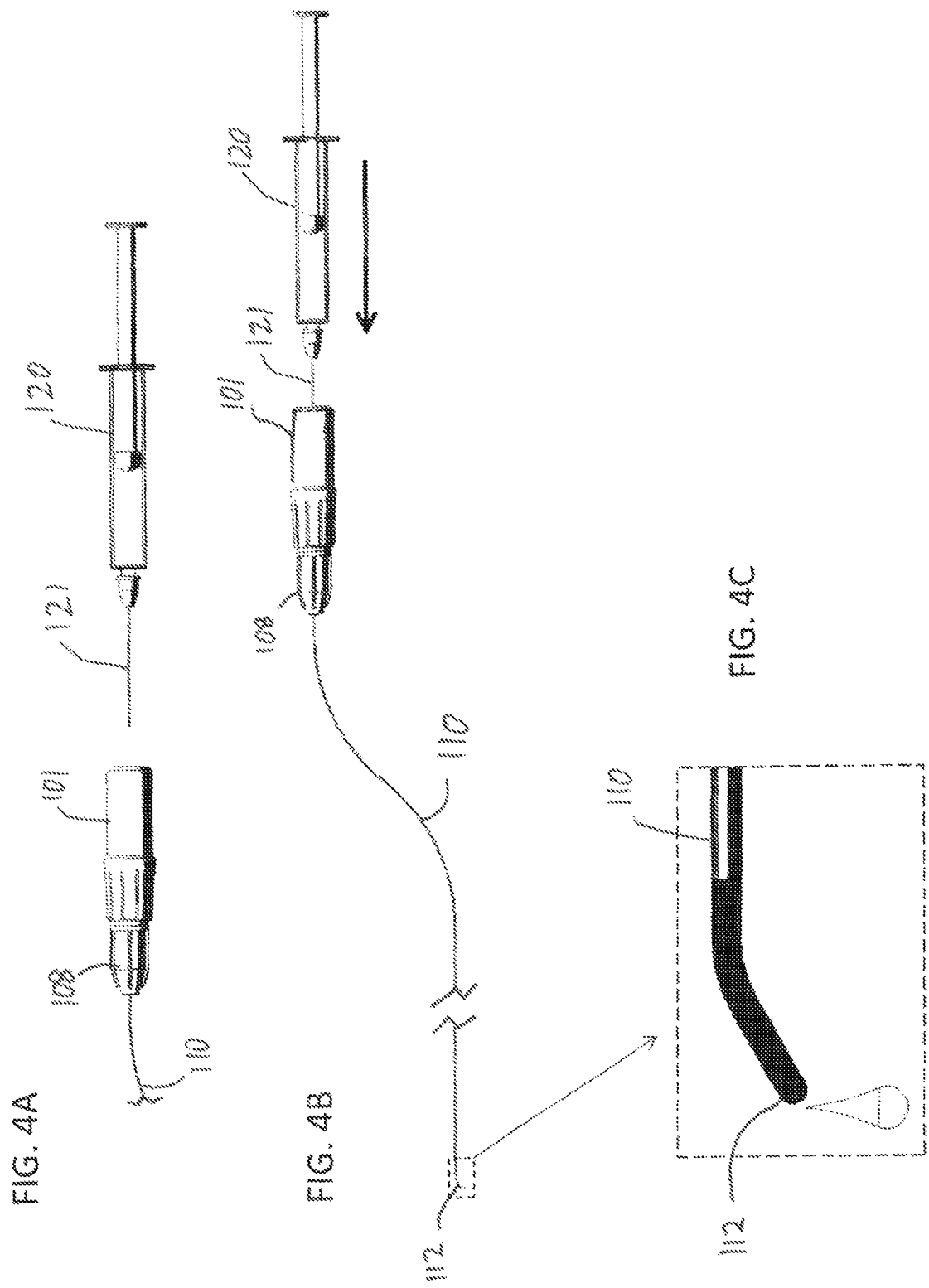

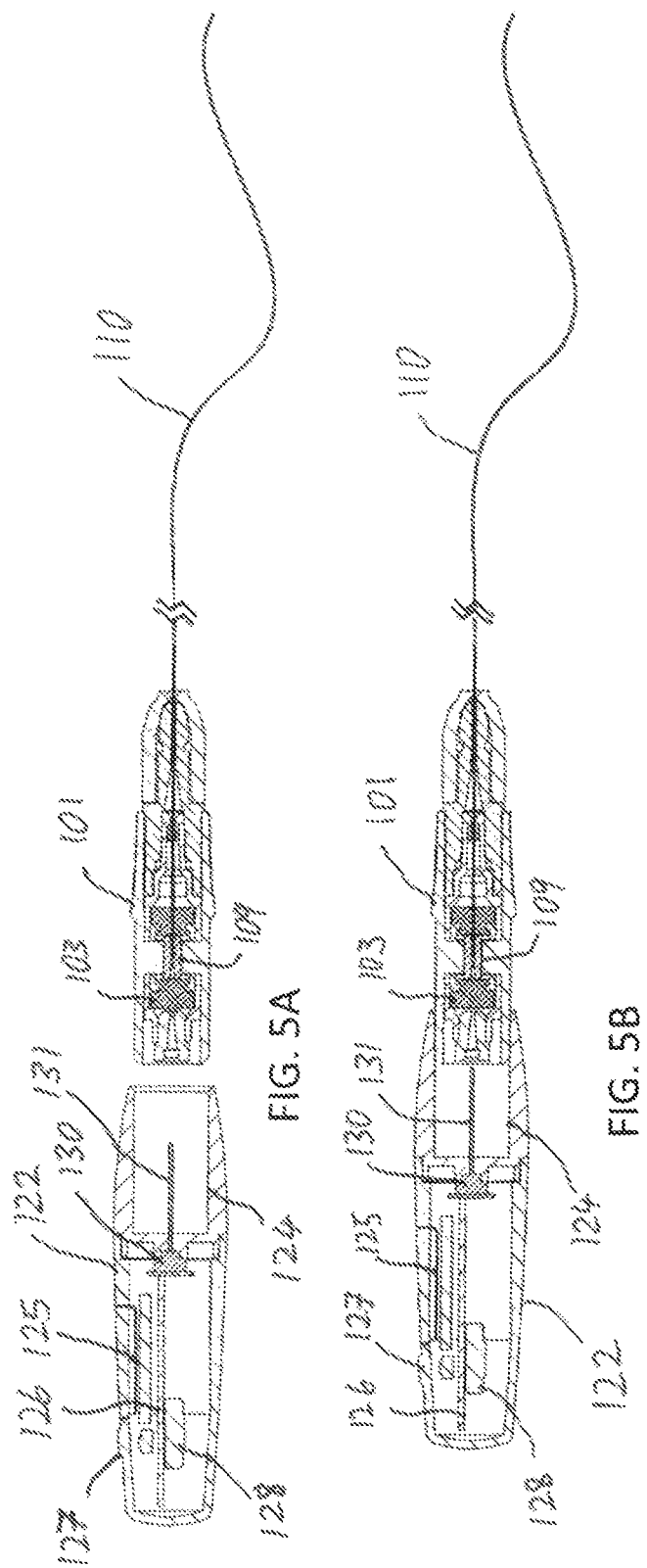

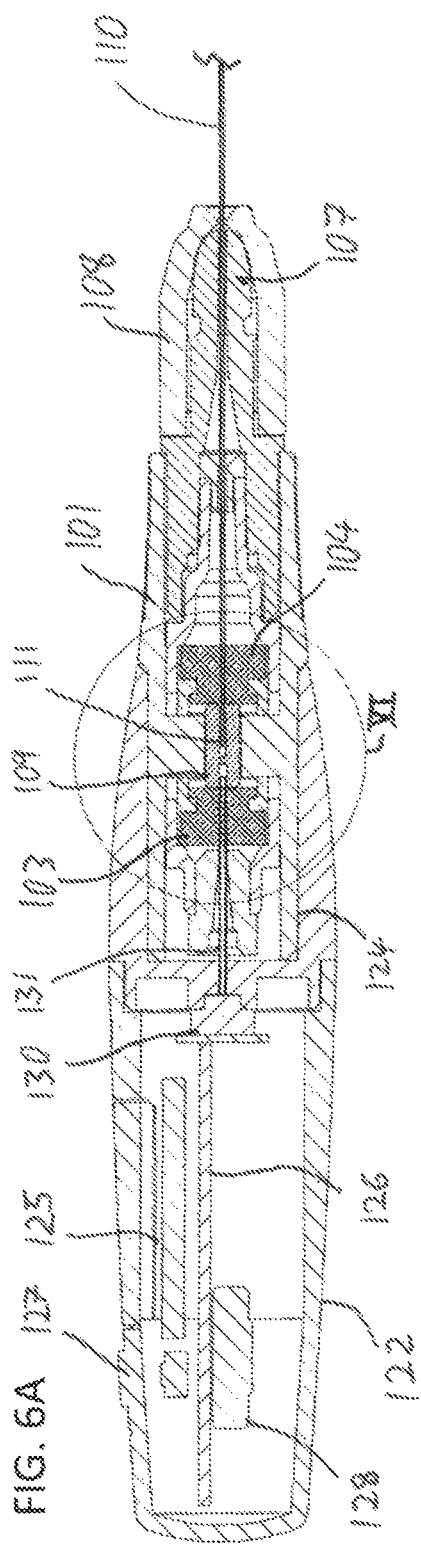
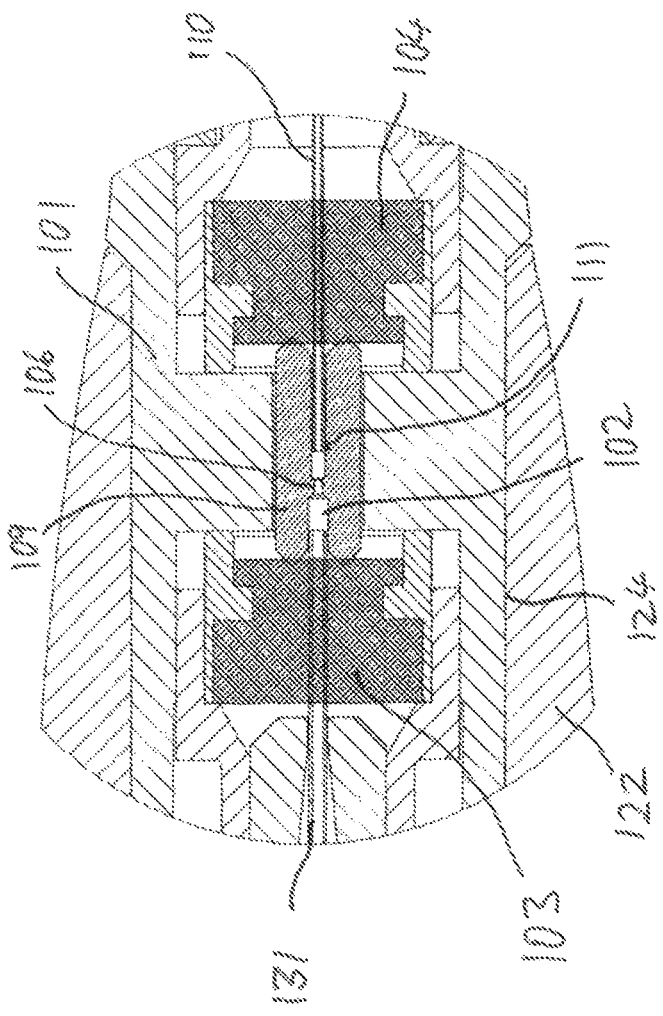
FIG. 6A
FIG. 6B

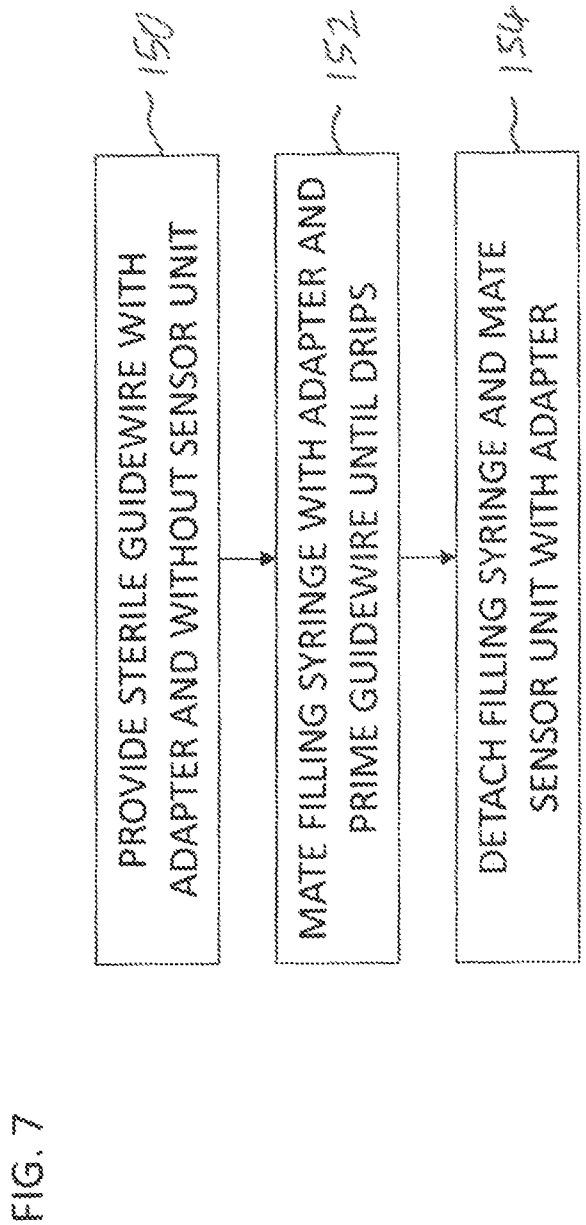

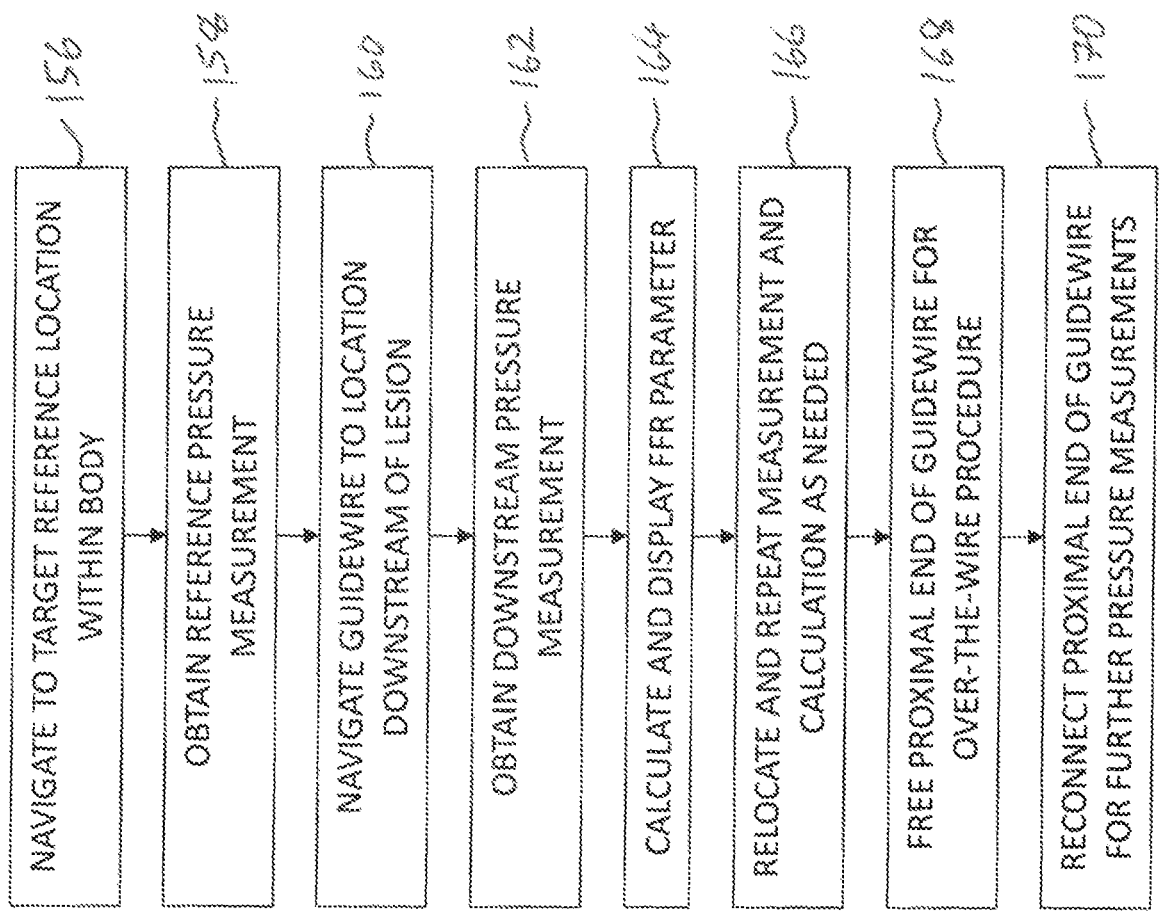

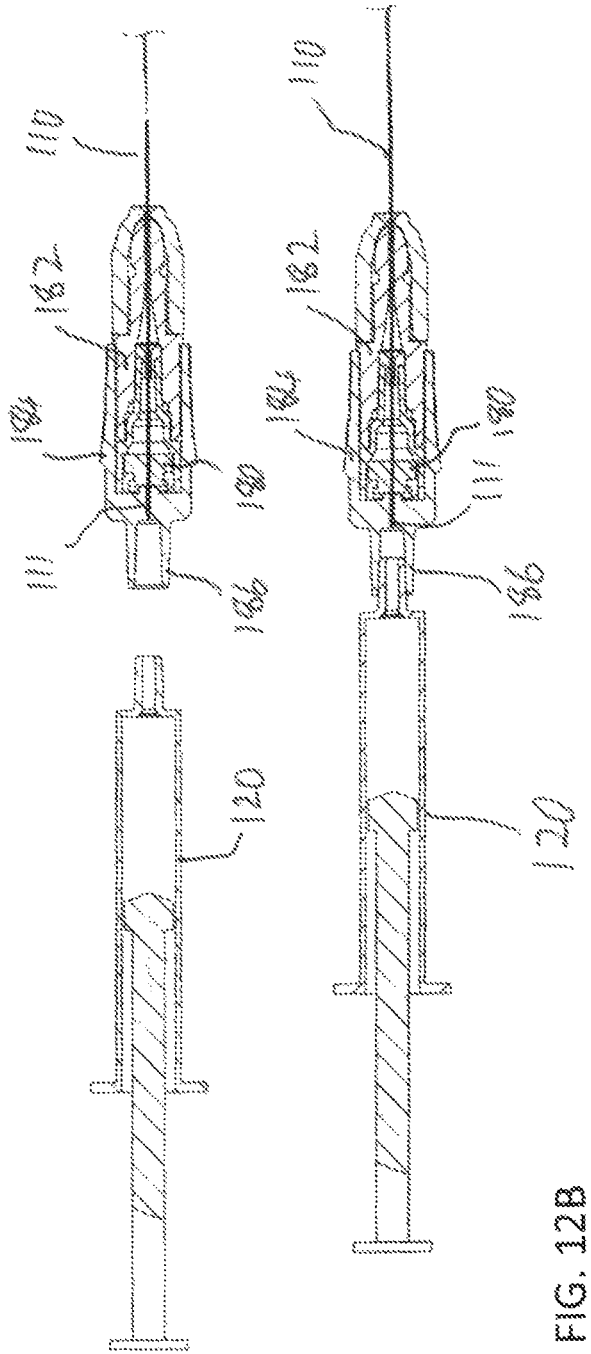

GUIDEWIRE SYSTEM FOR INTRA-VASCULAR PRESSURE MEASUREMENT

FIELD AND BACKGROUND OF THE INVENTION

The present invention relates to guidewires for intra-vascular procedures and, in particular, it concerns a hydraulic guidewire system in which a pressure sensor located in a handle outside the body senses intra-vascular pressure via a column of liquid within a lumen of the guidewire.

Measurement of pressure drop across an arterial stenosis has become an important diagnostic tool for assessing the actual impact of a stenosis on blood flow, or for identifying which of a number of stenoses require intervention. In order to facilitate deployment of a stent where needed, it is particularly advantageous for the pressure measurement to be performed using a guidewire which is compatible with a balloon/stent catheter according to the normal standards of Percutaneous Transluminal Coronary Angioplasty (PTCA) procedures. Therefore it is of an advantageous to use pressure measuring guidewires that are compatible with the standard PTCA 0.014" equipment, i.e., with an external guidewire diameter of 0.36 mm.

Pressure measuring guidewires that are compatible with the standard PTCA 0.014" equipment typically employ electro-mechanic sensors components located at the distal end of guidewire and connected to a signal processing unit by a thin long conductor along the guidewire. Such devices require sophisticated signal processing electronics in order to overcome measuring problems such as low signal to noise ratio that are associated with this structure. In order to simplify the device and to reduce its cost, it has been proposed to locate the pressure sensor external to the patient body and use a hollow guidewire filled with liquid media to make a hydraulic connection between the sensor and the vessel where the distal end of the guidewire is located.

In order to accurately measure the pressure in a fast and responsive manner, the volume between the sensor and the tip of the hollow wire should preferably be substantially filled with incompressible fluid, such as water or saline solution, without entrapped air bubbles. Air bubbles damp the system, since they require considerable flow of fluid along the guidewire lumen when the distal aperture is exposed to a pressure variation in order to compress or expand the bubble and equalize pressure at the transducer. This greatly impedes speed and accuracy of measurement. It is therefore important to remove air bubbles from the guidewire before it is introduced to the vessel.

Handling and storing a pre-filled guidewire raises problems of how to sterilize the device; how to maintain sterility; and how to prevent evaporation during storage. If the guidewire is to be provided without the liquid filling, it become problematic to perform priming of a long capillary lumen without applying sufficient pressure to damage the sensitive pressure sensor, and without leaving disruptive air bubbles in the connection to the pressure sensor, which would impact the accuracy and responsiveness of measurements.

More specifically, the lumen of a guidewire is necessarily very thin (located within the 0.36 mm diameter of the guidewire) and has a length of the order of 1.8 meters. In order to effectively flush the guidewire, the pressure at its connector is typically increased to at least several atmospheres and typically considerably higher. In order to accurately measure the pressures within the aorta and the coronary vessels, the pressure transducer should be very sensitive in the range of 70 to 140 mmHg (0.092 to 0.184 ATM). Commercially available transducers of a type suitable for performing such measurements, such as for example Measurements Specialists model MS5401-AM, cannot withstand pressures above 5 ATM, and are likely to be damaged by the pressures developed during flushing of the guidewire lumen.

SUMMARY OF THE INVENTION

The present invention is a pressure-measuring guidewire system in which a pressure sensor located in a handle outside the body senses intra-vascular pressure via a column of liquid within a lumen of the guidewire, and associated methods.

According to the teachings of an embodiment of the present invention there is provided, a pressure-measuring guidewire system comprising: (a) a hollow guidewire having a central lumen extending along a length of the guidewire; (b) a connector in sealed interconnection with a proximal end of the hollow guidewire, the connector having a contained volume that is in fluid connection with the central lumen of the hollow guidewire, the contained volume being bordered on at least one side by a septum; and (c) a pressure sensor comprising a transducer deployed for sensing a pressure within a sensing cavity, the pressure sensor including a hollow needle in fluid connection to the sensing cavity such that, when the hollow needle is inserted to penetrate the septum, the sensing cavity is brought into fluid connection with the contained volume of the connector and with the lumen of the guidewire.

According to a further feature of an embodiment of the present invention, the sensing cavity is substantially filled with a non-volatile fluid.

According to a further feature of an embodiment of the present invention, at least part of the hollow needle contains an air bubble.

According to a further feature of an embodiment of the present invention, the connector further comprises a second septum, the proximal end of the hollow guidewire being inserted so as to penetrate through the second septum to connect with the contained volume.

According to a further feature of an embodiment of the present invention, the connector further comprises a releasable clamp for clamping the hollow guidewire with the proximal end of the hollow guidewire inserted through the second septum.

According to a further feature of an embodiment of the present invention, the connector further comprises a constriction formed in the contained volume so as to prevent collision between the hollow needle and the proximal end of the hollow guidewire.

According to a further feature of an embodiment of the present invention, there is further provided: (a) a processing system comprising at least one processor, the processing system being electrically connected to the transducer so as to receive an output of the transducer; (b) a display associated with the processing system; and (c) a user input associated with the processing system, wherein the processing system is responsive to the user input and configured to: (i) in response to a first user input, record a pressure corresponding to a pressure at a first position of a distal tip of the guidewire; (ii) in response to a second user input, record a pressure corresponding to a pressure at a second position of a distal tip of the guidewire; and (iii) display on the display at least one parameter indicative of a relationship between the pressures at the second position and at the first position.

According to a further feature of an embodiment of the present invention, the pressure sensor, the processing system, the display and the user input are all provided carried by a single housing, the single housing being configured for selectively mating with the connector.

According to a further feature of an embodiment of the present invention, the guidewire comprises an elongated flexible shaft having a terminal portion terminating at a distal tip, wherein the terminal portion comprises a helical spring surrounding a central channel, and wherein the distal tip is an open distal tip defining an opening aligned with the central channel, the central lumen being contiguous with the central channel and extending to the open distal tip.

According to a further feature of an embodiment of the present invention, the open distal tip is formed by an end of the helical spring.

According to a further feature of an embodiment of the present invention, a flexible coating circumscribes the helical spring along a majority of a length of the terminal portion.

According to a further feature of an embodiment of the present invention, a length of the helical spring is at least about 10 centimeters.

There is also provided according to the teachings of an embodiment of the present invention, a method comprising the steps of: (a) providing the aforementioned system; (b) while the pressure sensor is disconnected from the connector, introducing via a filling needle inserted through the septum a biocompatible fluid under sufficient pressure to fill the contained volume and the central lumen with the biocompatible fluid; and (c) subsequent to the introducing, inserting the hollow needle to penetrate the septum, thereby bringing the sensing cavity of the pressure sensor into fluid connection with the fluid-filled lumen of the guidewire.

There is also provided according to the teachings of an embodiment of the present invention, a pressure-measuring guidewire system comprising: (a) a hollow guidewire having a central lumen extending along a length of the guidewire from a proximal end to a distal opening; (b) a pressure sensor comprising a transducer deployed for sensing a pressure within a sensing cavity, the sensing cavity being in fluid connection with a septum, the proximal end of the guidewire being deployed penetrating the septum such that the central lumen of the hollow guidewire is brought into fluid connection with the sensing cavity.

According to a further feature of an embodiment of the present invention, there is also provided a releasable clamp for clamping the hollow guidewire with the proximal end of the hollow guidewire inserted through the septum.

There is also provided according to the teachings of an embodiment of the present invention, a pressure-measuring guidewire system comprising: (a) a hollow guidewire having a central lumen extending along a length of the guidewire; (b) a pressure sensor in fluid connection with the central lumen of the hollow guidewire, the pressure sensor comprising a transducer deployed for sensing a pressure within the central lumen of the guidewire, wherein the guidewire comprises an elongated flexible shaft having a terminal portion terminating at a distal tip, wherein the terminal portion comprises a helical spring surrounding a central channel, and wherein the distal tip is an open distal tip defining an opening aligned with the central channel, the central lumen being contiguous with the central channel and extending to the open distal tip.

According to a further feature of an embodiment of the present invention, the open distal tip is formed by an end of the helical spring.

According to a further feature of an embodiment of the present invention, a flexible coating circumscribes the helical spring along a majority of a length of the terminal portion.

According to a further feature of an embodiment of the present invention, a length of the helical spring is at least about 10 centimeters.

According to a further feature of an embodiment of the present invention, the hollow guidewire has a length and an external diameter, the length being in excess of 1000 times the external diameter, and wherein the hollow guidewire is flexible and configured for use in a percutaneous coronary intervention.

BRIEF DESCRIPTION OF THE DRAWINGS

The invention is herein described, by way of example only, with reference to the accompanying drawings, wherein:

FIGS. 2A-2C are an isometric view, side view and plan view, respectively, of a pressure-measuring guidewire system according to a further aspect of the present invention;

FIG. 3 is a plan view of the system of FIG. 2A in a storage configuration prior to use;

FIGS. 4A and 4B are successive side views illustrating stages of priming of the system of FIG. 2A using a syringe, prior to mating with a pressure-sensor unit;

FIG. 4C is an enlarged detail of FIG. 4B in the region marked by a dashed rectangle;

FIGS. 5A and 5B are axial cross-sectional views taken through the system of FIG. 2A showing the guidewire connector before and during mating with the pressure-sensor unit;

FIG. 6A is an axial cross-sectional views taken through the system of FIG. 2A showing the guidewire connector fully mated with the pressure-sensor unit;

FIG. 6B is an enlarged detail of the region of FIG. 6A designated VI;

FIG. 7 is a flow diagram illustrating the steps in preparing the system of FIG. 2A for use;

FIG. 8 is a flow diagram illustrating a sequence of operation of the system of FIG. 2A;

FIGS. 12A and 12B are axial cross-sectional views before and after connection of a priming syringe, illustrating how priming is performed for the variant implementation of FIG. 11A.

DESCRIPTION OF THE PREFERRED EMBODIMENTS

The present invention is a pressure-measuring guidewire system in which a pressure sensor located in a handle outside the body senses intra-vascular pressure via a column of liquid within a lumen of the guidewire, and associated methods.

The principles and operation of systems and methods according to the present invention may be better understood with reference to the drawings and the accompanying description.

By way of introduction, the novel features of the present invention may be subdivided into two distinct sets of features which are each considered of patentable significance in their own right, but which are most preferably used together in a particularly preferred embodiment of the present invention. A first set of features relates to a distinctive implementation of a distal portion of a hydraulic pressure-sensing guidewire according to a first aspect of the present invention, as will be detailed with reference to FIG. 1. A second set of features relates to various aspects of the connection between a pressure sensing device and a proximal end of the guidewire, aspects of the implementation of the sensor unit, and the manner of preparing the guidewire for use, all as will be described with reference to FIGS. 2A-10. Although the scale of the illustrations for FIGS. 2A-10 do not permit illustration of the details of the distal portion of the guidewire, it should be noted that the preferred implementation of the guidewire in each case is as illustrated and described with reference to FIG. 1.

Figure 1:
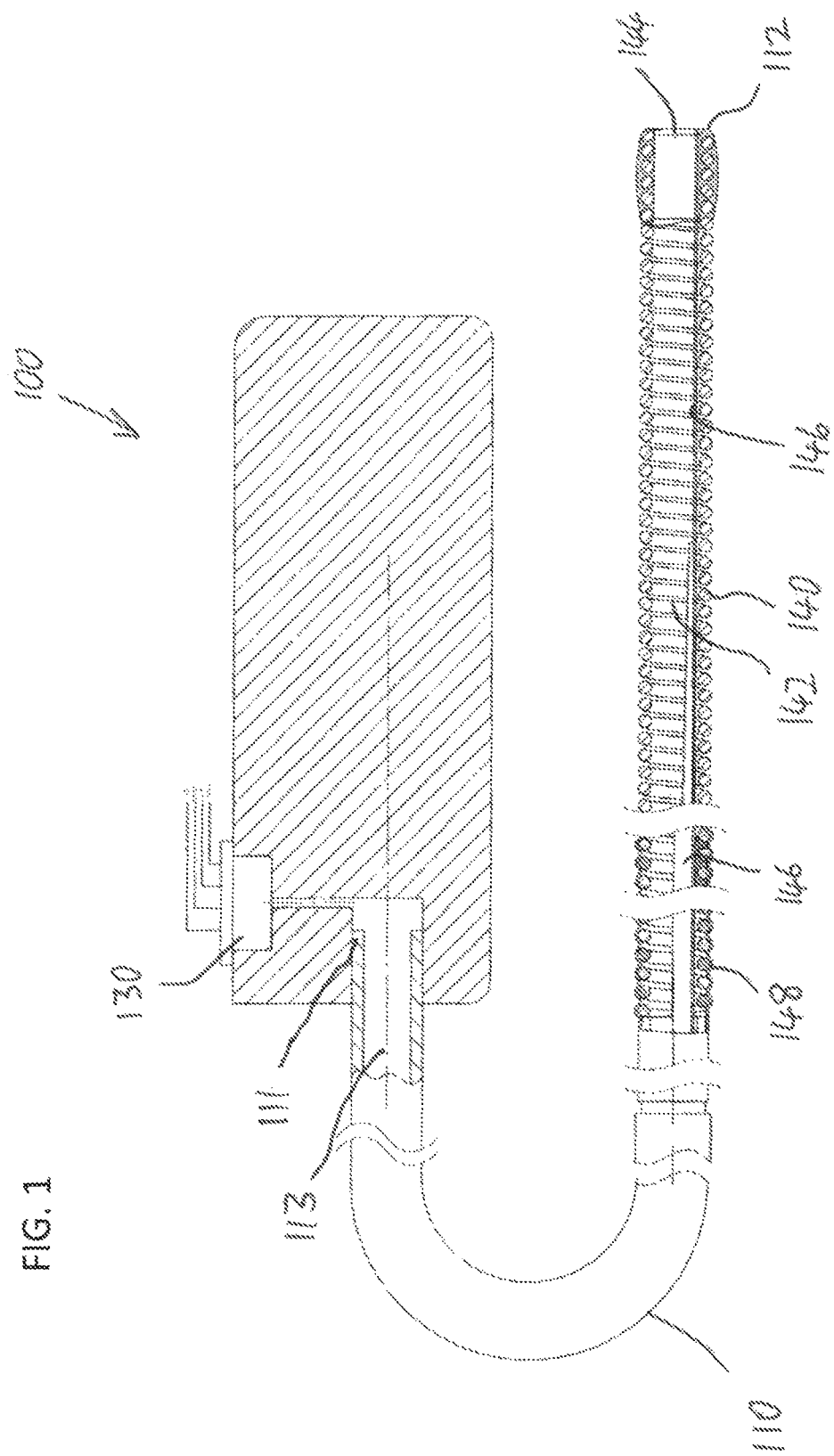
FIG. 1 is a schematic axial cross-sectional view taken through a pressure-measuring guidewire system according to an aspect of the teachings of the present invention, showing details of a preferred implementation of a terminal portion of the guidewire.
Figure 2A:
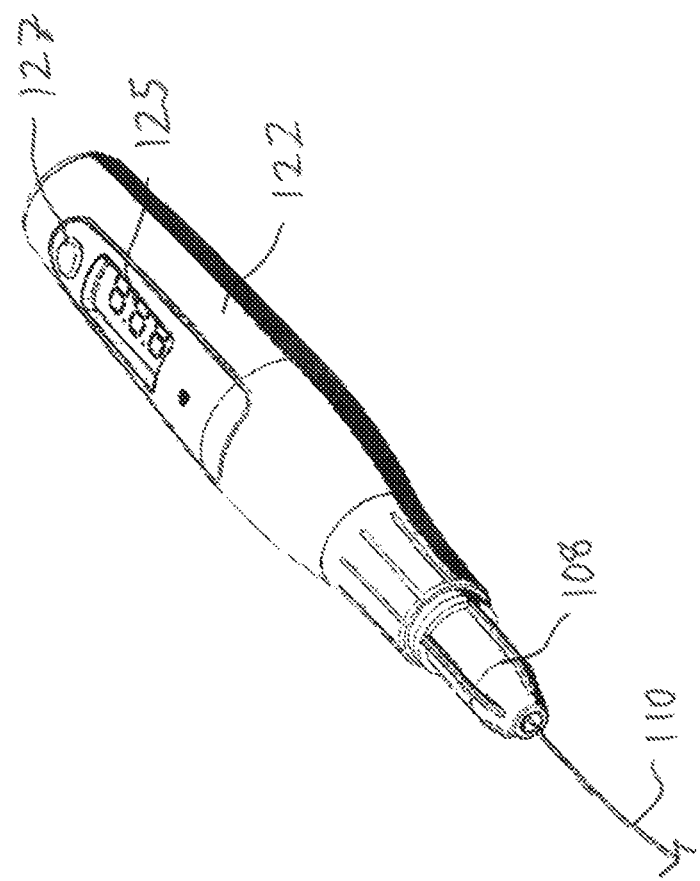
Figure 4D:
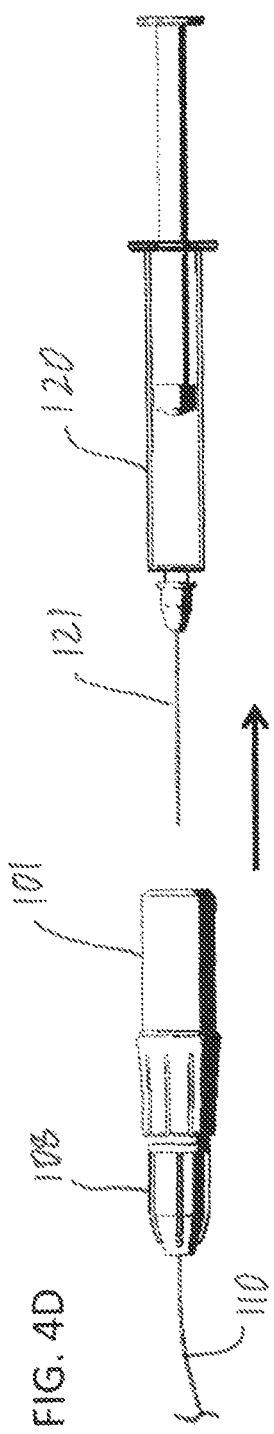
FIGS. 4D-4F are successive side views illustrating removal of the priming syringe and mating of a guidewire connector with a pressure-sensor unit.
Figure 4E:
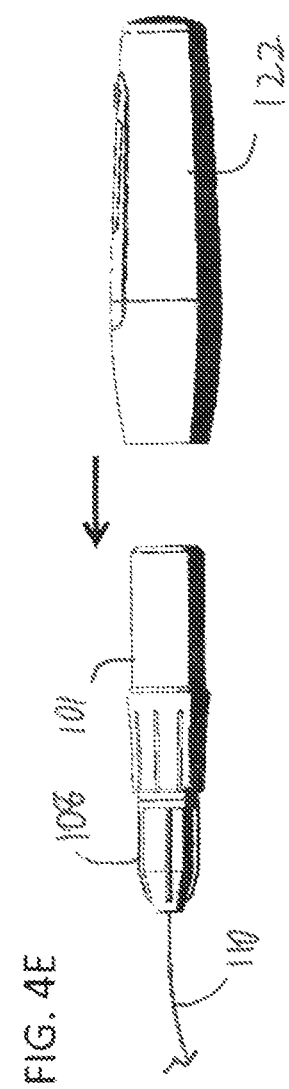
Figure 4F:
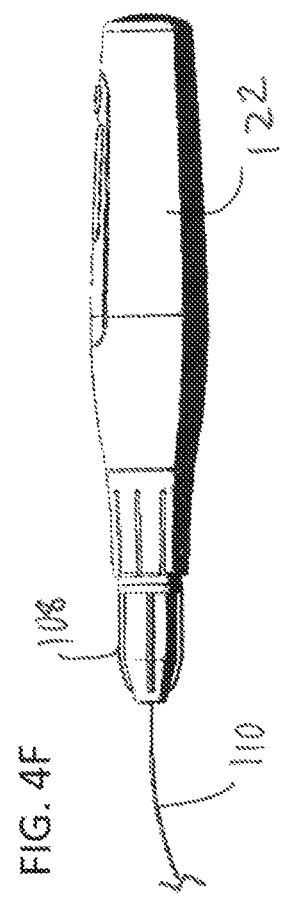

Turning now to the first aspect of the present invention, FIG. 1 illustrates schematically a pressure-measuring guidewire system, generally designated 100, constructed and operative according to an aspect of the present invention. Generally speaking, system 100 includes a hollow guidewire 110 having a central lumen 113 extending along a length of the guidewire from a proximal end 111 to a distal end 112. A pressure sensor, provided in fluid connection with central lumen 113 of the hollow guidewire, includes a transducer 130 deployed for sensing a pressure within central lumen 113 of the guidewire. Guidewire 110 has an elongated flexible shaft including a terminal portion terminating at distal tip 112. The terminal portion includes a helical spring 140 surrounding a central channel 142, and distal tip 112 is an open distal tip defining an opening 144 axially aligned with central channel 142. Central lumen 113 extends throughout the length of guidewire 110, being contiguous with central channel 142 and extending to open distal tip 112. Open distal tip 112 can most simply be implemented as shown here as an end of helical spring 140, typically with the last few coils welded together and attached to the end of a tapered internal support 146, provided to ensure safety against intra-body fracture of the spring and providing graduated flexibility of the guidewire such that the flexibility increases along the terminal portion towards the distal tip.

It should be noted that use of an open-tipped helical spring to provide hydraulic connection for pressure measurement marks a pronounced divergence from the conventional approaches to hydraulic pressure-measurement guidewires. Specifically, this structure provides mechanical properties fully equivalent to those of a conventional coronary guidewire, resulting from the combination of the helical spring structure extending at least 10, and more preferably about 15, centimeters, with graduated variation of flexibility as provided by tapered internal support 146. The result is a mechanical structure which is highly flexible in a transverse direction, can support considerable axial compression forces to push its way through lesions, and which can maintain a manually set curvature induced manually by a practitioner prior to insertion. At the same time, the open distal tip provides an effective hydraulic linkage to the intravascular fluids with minimal additional fluid flow impedance. This differs markedly from alternative approaches proposed in the literature which employ either lateral apertures proximal to a helical spring tip, requiring shortening of the spring, or modifications of the spring itself to ensure openings between the coils, which either adversely affects the properties of the spring or adds significant extra fluid flow impedance, which impacts the effectiveness of the measurements, or both of the above.

In order to ensure that the lumen 113 extends to the vicinity of the distal tip without pressure leakage of through coils of the helical spring, a flexible coating 148 preferably circumscribes the helical spring 140 along a majority of a length of the terminal portion. The flexible coating may be of any suitable flexible biocompatible polymer layer which creates a fluid barrier around the helical spring coils without significantly impacting the flexibility properties of the terminal portion of the guidewire. The flexible coating most preferably stops short of the distal tip by between about 10 to about 40 millimeters, thereby avoiding any potential adverse effect on the highly flexible properties of the distal tip region. Any hydraulic coupling that might occur via spaces between the coils of the helical wire in this distal tip region is typically insignificant relative to the large distal tip opening, and in any case, is sufficiently close to the tip that it is typically advanced beyond the relevant lesion prior to pressure measurement, and is therefore exposed to the same pressure as is present at the tip.

The depiction of pressure sensor transducer 130 in FIG. 1 is only schematic, and does not present all details of a practical pressure sensor design. The form of connection between the hydraulic guidewire and the pressure sensing arrangement may be according to any known configuration for pressure sensing via a hydraulic guidewire. In a particularly preferred but non-limiting set of embodiments, the form of connection may advantageously be implemented according to the teachings of the further aspects of the present invention described below.

Turning now to FIGS. 2A-10, there are shown various aspects of a pressure-measuring guidewire system, constructed and operative according to a certain non-limiting but particularly preferred embodiment of the present invention. The guidewire system includes a hollow guidewire 110 having a central lumen extending along a length of the guidewire from a proximal end 111 to a distal end 112. The central lumen and other structural details of the guidewire are not separately visible at the scale of these drawings, but are most preferably implemented according to the structural details of guidewire 110 described above with reference to FIG. 1. A connector 101 is deployed in sealed interconnection with proximal end 111 of hollow guidewire 110 so that the central lumen of the guidewire is in fluid connection with a contained volume 102 within connector 101. Contained volume 102 is bordered on at least one side by a septum 103 and, in the non-limiting but preferred case illustrated here, also on a second side by a septum 104 detailed further below.

A pressure sensor implemented in a sensor unit 122 includes a transducer 130 deployed for sensing a pressure within a sensing cavity, the pressure sensor including a hollow needle 131 in fluid connection with the sensing cavity such that, when hollow needle 131 is inserted to penetrate septum 103, the sensing cavity is brought into fluid connection with the contained volume 102 of the connector, and hence with the lumen of guidewire 102.

According to one aspect of the present invention, precautions are taken to avoid damping by air bubbles in the hydraulic path from transducer 130 along the hollow guidewire 110, as will be detailed below. Firstly, sensing cavity of transducer 130 is preferably substantially filled with a non-volatile fluid. Air is preferably substantially eliminated by performing a degassing procedure through which the dead volume is filled with a non-volatile fluid, typically a gel or an oil. Degassing is typically achieved by immersing at least the opening of the transducer cavity in a quantity of the non-volatile fluid (non-evaporating gel or oil), and reducing the pressure around the device by application of vacuum from a vacuum pump. This draws out the gas from the cavity and, when the vacuum is released, the non-volatile fluid is drawn in to fill the cavity. Optionally, this process may be repeated as required. The term "non-volatile" is used herein in the description and claims to refer to a non-gaseous fluid (liquid or gel) which remains stable under normal atmospheric conditions for an extended period without noticeable evaporation. In intuitive terms, this means that a fluid filled cavity filled with such a non-volatile fluid will remain "fluid-filled" over a period typically required for the shelf-life of a commercial medical device, typically in excess of 12 months, without "drying out." A range off suitable non-volatile fluids are readily available, non-limiting examples including, for example, mineral oils.

It is typically not feasible and/or desirable to require sterility of the internal cavity of the transducer. It is, therefore, necessary to ensure that the fluid filling the transducer cavity does not come into contact with the filling fluid within the guide wire. This is preferably achieved by leaving a small "airlock" bubble within the septum needle 131 which connects pressure transducer 130 to the fluid column within the guide wire lumen. Because of the very small dimensions of the internal channel of the septum needle, the volume of the airlock bubble is sufficiently small (typically in the range of a microliter or less) that it does not impact the speed or accuracy of the pressure measurements, but it does form a buffer to prevent contact or mixing of the two fluids. This degassing process is preferably performed as part of the manufacturing process, so that the pressure sensor unit 122 is provided with the pressure sensor in its degassed state, but not necessarily sterile, while the guidewire 110 is typically provided pre-connected to connector 101, threaded into a protective shipping tube 129 (see FIG. 3) in a sterile package (not shown), in dry condition after undergoing a standard sterilization process such as ETO or Gama radiation exposure, as is known in the art.

Shortly prior to use, a biocompatible incompressible fluid, such as saline, is injected, typically by use of filling syringe 120, by inserting the cannula 121 of the filling syringe 120 through the proximal septum seal 103 (FIGS. 4A and 4B) and forcibly injecting the saline, thereby flushing air out of the internal volume 102 of the connector 101 and the interior lumen of the hollow guide wire 110 until a few drops of saline are seen to be released from the tip of the guidewire (FIG. 4C), indicating that priming of the system is complete. Cannula guiding features of connector 101 preferably guide cannula 121 to a central bore of a generally cylindrical sealing element 109 defining internal volume 102. A stopper 106 (FIG. 6B) is preferably formed as an internally projecting ridge or step within the central bore of sealing element 109 so as to form a limiter which prevents over-insertion of cannula 121 and the proximal end of guidewire 110. The stopper 106 allows enough space for introducing of the cannula 121 of the filling syringe 120 through the septum seal 103, while preferably preventing collision between cannula 121 and the proximal end 111 of guide wire 110.

Priming of the guidewire with fluid involves advancing a column of fluid along the very fine and long inner lumen of the guide wire, which requires relatively high pressure, but this is well within the range of pressures that can be generated by manual force applied to the plunger of a standard syringe. In a typical example, the internal lumen has an internal diameter of less than 0.3 mm and a length of over 1 meter, typically about 1.8 meters. Priming of such a capillary lumen with a water-based solution in a time effective manner may require a pressure of a few bar. Such pressures can readily be achieved by manual force applied to a standard syringe plunger.

After this priming procedure, cannula 121 of filling syringe 120 is withdrawn, and the pressure sensor transducer 130 is connected by inserting its cannula 131 through proximal septum 103 so that the pressure sensor is in hydraulic connection with the primed hollow guide wire 110. In the particularly preferred implementation illustrated here, sensor housing 122 is formed with a socket 124 sized to receive and guide a complementary-shaped outer surface of connector 101, thereby correctly guiding the insertion of cannula 131 through septum 103 and into sealing element 109. The aforementioned cannula guiding features of connector 101 also help ensure correct alignment of the cannula. The pressure sensing transducer 130 is then in fluid connection via the internal channel of sealing element 109 with the internal lumen of hollow guidewire 110, thus allowing pressure sensing of a pressure at the distal tip of the guidewire. The aforementioned steps for preparing the guidewire system for use, corresponding to a method according to the teachings of the present invention, are shown as steps 150, 152 and 154 in FIG. 7. The fact that the pressure sensor is not connected to the lumen during priming allows the user to flush the guide wire lumen with as much pressure as he or she can apply, without concern for causing damage to the transducer.

Turning now to the additional features and functions of the system, as best seen in FIG. 6A, the system preferably includes a processing system comprising at least one processor, represented here schematically as a circuit-board and processor combination 126, electrically connected to transducer 130 so as to receive an output from the transducer. A display 125 and a user input 127 (typically one or more manually operable buttons) are associated with the processing system, and the electronics subsystem is preferably powered by a small onboard battery 128. Optionally, the device may also have on the circuit board additional components for wireless communications, as will be discussed below. The processing system preferably includes various signal processing hardware (which may be implemented as analogue circuitry, digital processors or any combination thereof), software and/or firmware required to turn the signals from transducer 130 into a stable and reliable indication of pressure. The circuitry required for this purpose is typically provided built-in together with various commercially available pressure-measurement transducers that are suitable for pressure measurement in the range of pressures and with the degree of accuracy required for this application.

In addition to the transducer signal processing functions, the processing system is preferably additionally configured to be responsive to the user input and configured:

a. in response to a first user input, such as a long-press on a button 127, to record a pressure corresponding to a pressure at a first position of distal tip 112 of guidewire 110;
b. in response to a second user input, typically a subsequent short-press on a button 127, to record a pressure corresponding to a pressure at a second position of distal tip 112 of guidewire 110; and
c. to display on display 125 at least one parameter indicative of a relationship between the pressures at the second position and at the first position.

This latter parameter is most preferably the Fractional Flow Reserve (FFR) calculated as the pressure at the second location represented as a percentage of the pressure at the reference location, although other metrics may also be used. It will be understood that the "pressure measurement" referred to here is typically derivation of an average over several pulse cycles of the systolic blood pressure at the relevant locations.

Other modes of operation are also possible, for example, where a reference value for a baseline blood pressure is supplied from an external source, such as via wireless communication. The reference value may either be used instead of a measured value at the first location, or may be used in a calibration process in order to render individual pressure measurements of the device more reliable and/or precise.

In a particularly preferred implementation, all of the aforementioned components of the pressure sensor, the processing system, the display and the user input are mounted in or on a single housing (unit 122) configured for selectively mating with connector 101. The system thus provides a stand-alone device for intravascular pressure and/or FFR measurement which can be operated autonomously without requiring expensive integration with other operating room equipment.

A typical sequence of operation of the system (subsequent to the priming process described above) is illustrated in FIG. 8. The guidewire is first navigated to a target reference location within the body where the first (reference) pressure is to be measured, typically proximal to a lesion to be assessed (step 156), and the user actuates measurement of the reference pressure value, such as by a long-press on an actuation button 127 (step 158). The tip of the guidewire is then navigated to a location downstream from the lesion, typically passing the lesion (step 160), and the user actuates the button to sample a second pressure reading (step 162), which results automatically in calculation of the FFR measurement which is displayed on display 25 (step 164). If further FFR measurements are required, the guidewire can be relocated and the measurement and calculation repeated as desired (step 166).

To allow the delivery of a balloon/stent catheter over the wire, the connector 101 can preferably be removed from the hollow guide wire 110 by unlocking the clamping arrangement (in this example, by loosening a locking nut 108 so as to release the clamping force of a collet 107) and pulling the end of the wire 111 out of the distal septum seal 103. A balloon/stent catheter or other over-the-wire device can then be threaded onto the guidewire and advances along the guidewire so as to reach the desired intrabody location for performance of a procedure (step 168). The arrangement described herein allows the user to subsequently reinstall the connector to the proximal end of the hollow guide wire 111. Reattachment of connector again allows pressure measurement using sensor 130 so that the user can return to the FFR measurement process, for example, to assess the post-procedural pressure drop across the treated region of a blood vessel, or to assess the need for treatment of additional lesions (step 170). This detachment and reattachment of the guidewire is illustrated schematically in FIG. 10.

Similarly, the sensor unit 111 can be removed and/or reinstalled on the connector 101 such that the user is able to use the wire with or without the sensor unit, according to his or her preference and convenience.

Since transducer 130 is introduced to the connector after the priming, there is also no chance that the flushing fluid would carry infective bodies from the transducer to the distal end of the wire during the priming process.

As already mentioned, the cannula 131 of transducer 130 is preferably filled with non-volatile fluid, such as oil. A tiny bubble of air (much smaller than the dead volume of prior art sensors, and typically less than about 1 microliter) is formed at the tip of the cannula when introducing the cannula to the port of the connector. This bubble acts as a barrier between the oil and the medium in the fluid line, a barrier that prevents potential infection of the device also during this detachment and reconnection process.

In summary, the guide wire device described herein preferably addresses the need for a pressure measuring guide wire that is 0.014" compatible; preferably having a simple and cheap sensor located at its proximal end external to the patient body; is preferably supplied in a dry sterile condition and provides a convenient filling process that does not leave air bubbles; and preferably allows the user to prime the guide wire with biocompatible sterile fluid without the risk of damaging the pressure sensor during this process; and assures that there is no chance that the flushing fluid would carry infective bodies from the transducer to the distal end of the wire during the priming process.

Figure 9:
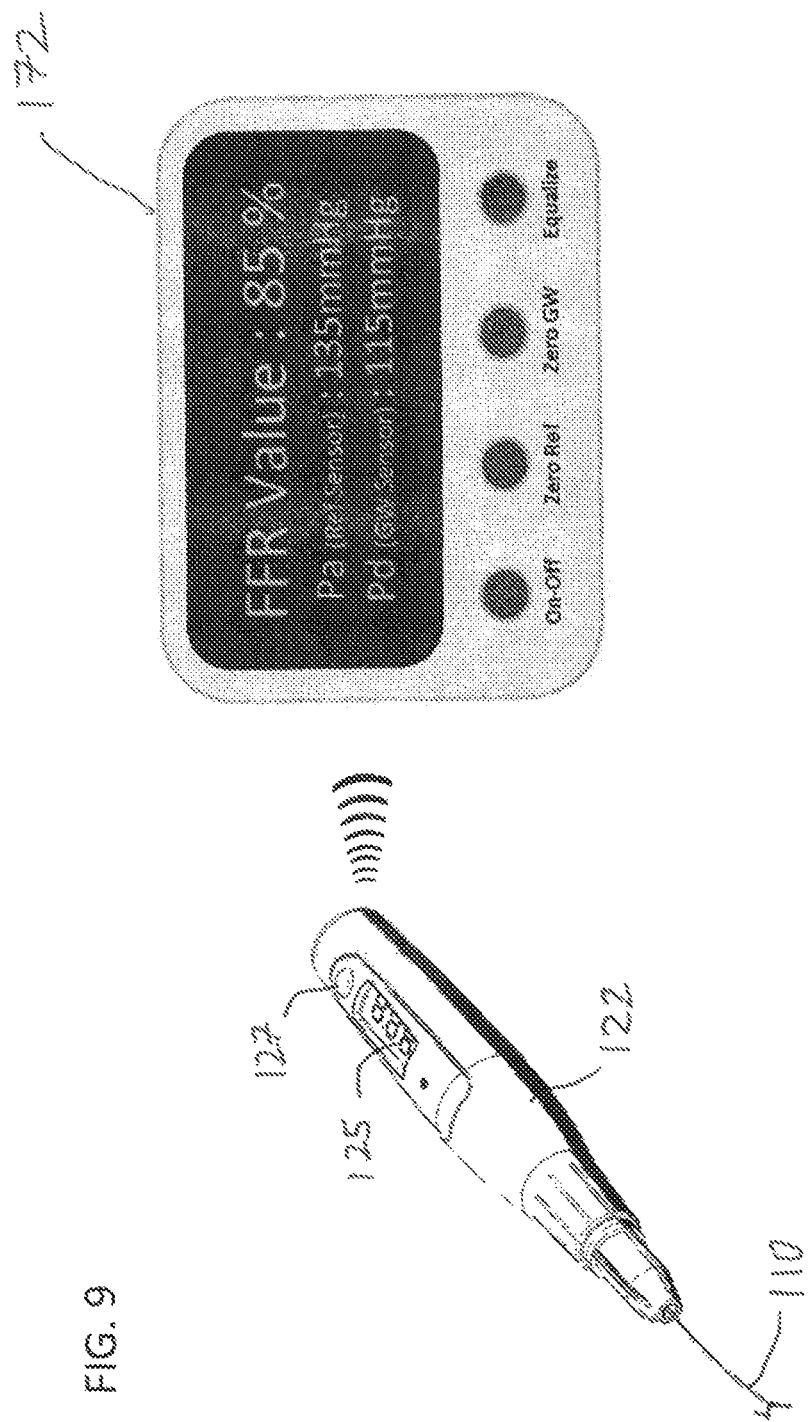
FIG. 9 is a schematic isometric view of the system of FIG. 2A used together with a wireless monitor and remote controller.
Figure 10:
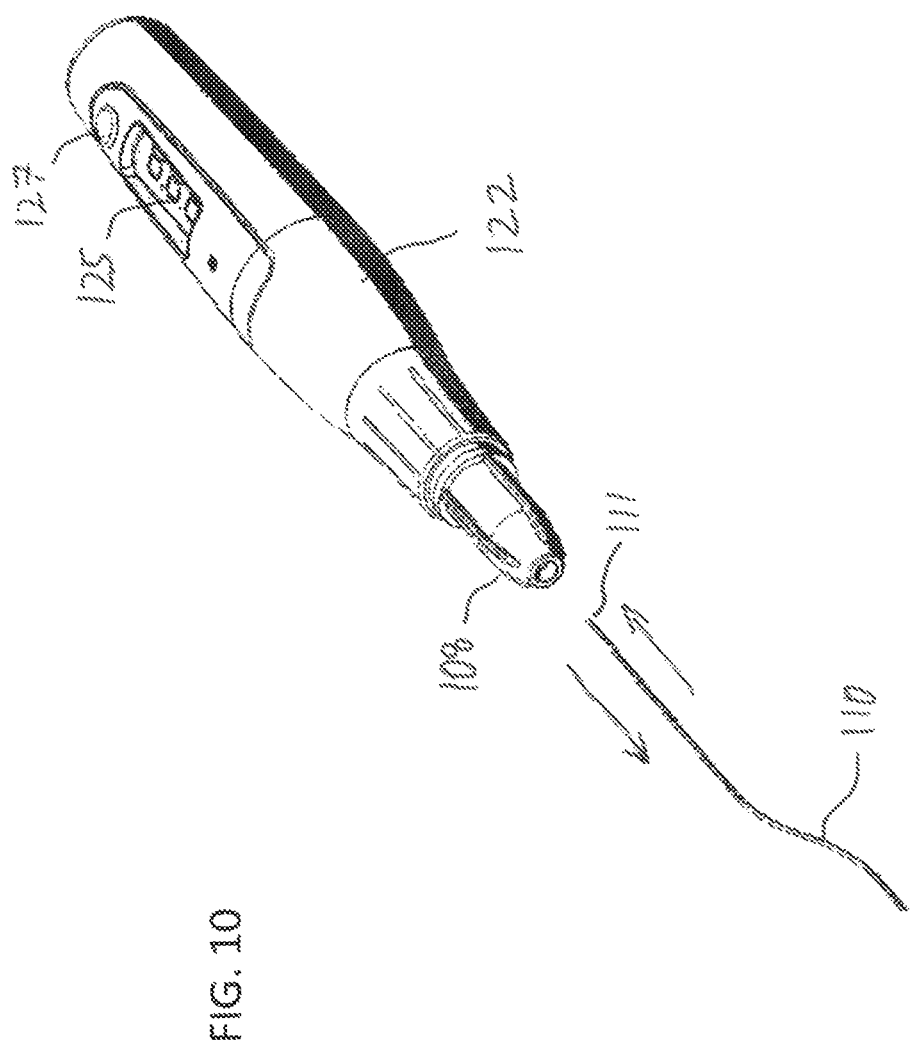
FIG. 10 is a schematic isometric view of the system of FIG. 2A illustrating disconnection and reconnection of the guidewire from and to the sensor unit, to facilitate performance of an over-the-wire procedure followed by further pressure measurement.

Referring now to FIG. 9, although the system is preferably implemented as a stand-alone system which can be used without integration with other equipment, it may in some cases be advantageous to provide a remote unit for displaying the output information and/or actuating pressure measurements. FIG. 9 illustrates one such case, where wireless communication components within unit 122 communicate through one-directional or bidirectional communication with a remove display or display/control unit 172. The display and functions of any inputs of unit 172 preferably parallel the functions of unit 122 described above.

Figure 11A:
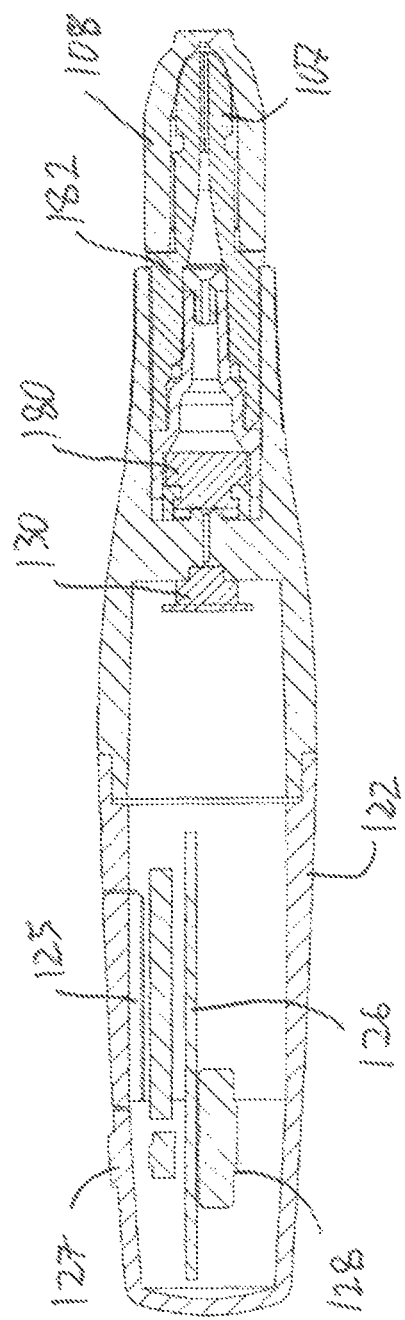
FIGS. 11A and 11B are axial cross-sectional views taken through a variant of the system of FIG. 2A, before and after insertion of the guidewire, respectively.
Figure 11B:
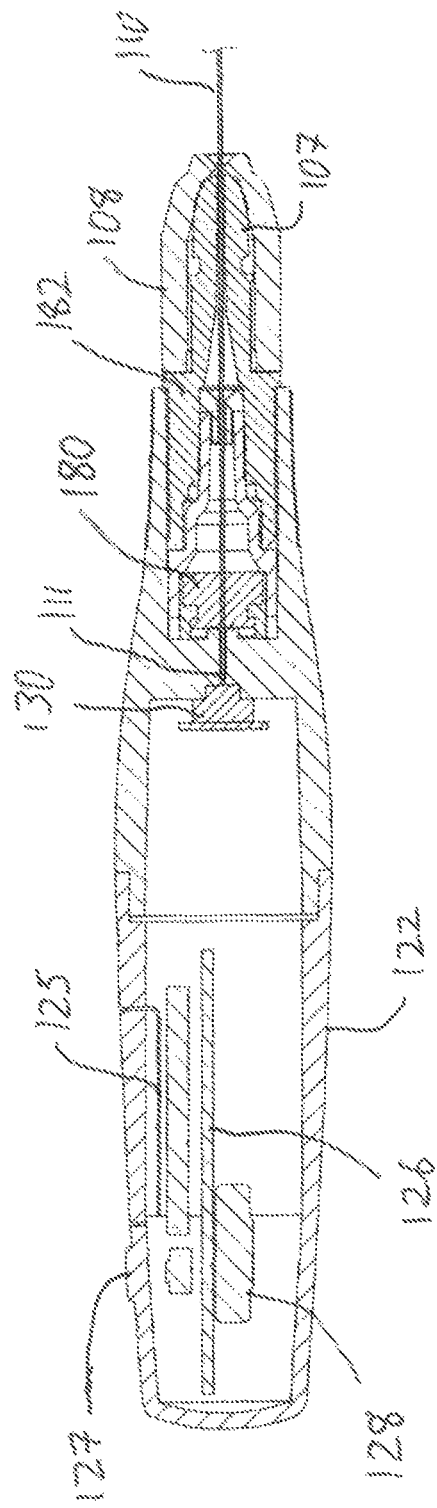

Turning now to FIGS. 11A-12B, it should be noted that similar functionality to that described above can, in some cases, be achieved by using an arrangement with a single septum, where penetration of the proximal tip 111 of guidewire 110 is used directly to connect to a sensing cavity of a transducer 130. One such non-limiting implementation is illustrated in FIGS. 11A and 11B.

Specifically, the device as illustrated here is generally similar to the device illustrated above, with equivalent elements labeled similarly. This device differs from the device described above primarily in that the pressure sensing transducer 130 is here not associated with a cannula, but instead faces a sensing cavity into which proximal end 111 of guidewire 110 penetrates directly via a single septum 180. Septum 180 is preferably supported by a connector 182 which provides guiding features for correctly aligning the end of the guidewire, as described above, as well as releasable clamping features (nut 108 and collet 107) also preferably as described above.

Priming of the guidewire according to this option is typically performed as illustrated in FIGS. 12A and 12B by providing an adapter 184 with a Luer connector 186 or other suitable interface to allow connection of filling syringe 120 via adapter 184 to connector 182, and thus providing fluid connection to the inner lumen of guidewire 110 once inserted through septum 180.

In all other respects, the structure and function of this variant of the present invention will be fully understood by reference to the above description.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. A method of preparing a pressure-measuring guidewire system for use, the method comprising the steps of:
   (a) providing a hollow guidewire having an inner lumen, said guidewire being provided in a dry, sterile state;
   (b) providing a pressure sensor having a transducer deployed for sensing a pressure within a sensing cavity, said sensing cavity being at least partially filled with a non-volatile fluid;
   (c) while said hollow guidewire is disconnected from said pressure sensor, introducing into said inner lumen of said guidewire an incompressible biocompatible fluid under sufficient pressure to fill said inner lumen with said biocompatible fluid; and
   (d) subsequent to said introducing, mating said hollow guidewire with said pressure sensor so as to bring said sensing cavity of said pressure sensor into fluid connection with said inner lumen of said guidewire,
wherein said mating is performed with a proximal end of said hollow guidewire inserted into a central bore within a connector, said central bore defining an internal volume and having a stopper to limit insertion of said hollow guidewire, said mating being performed so as to avoid contact between said non-volatile liquid and the biocompatible fluid by leaving an air bubble between the biocompatible fluid and said non-volatile fluid.

2. The method of claim 1, wherein said air bubble between the biocompatible fluid and said non-volatile fluid has a volume of no more than 1 microliter.

3. The method of claim 1, wherein said contained volume is bordered by a septum, and wherein said pressure sensor has a hollow needle, said mating including penetrating said septum with said hollow needle so as to bring a tip of said hollow needle into said contained volume.

4. A pressure-measuring guidewire system comprising:
   (a) a hollow guidewire having an inner lumen, said guidewire being packaged in a dry, sterile state;
   (b) a pressure sensor having a transducer deployed for sensing a pressure within a sensing cavity, said sensing cavity being at least partially filled with a non-volatile fluid; and
   (c) a connector having a central bore defining an internal volume, said internal volume being in fluid connection with said sensing cavity of said pressure sensor, said central bore having a stopper configured such that, when said inner lumen of said hollow guidewire is filled with an incompressible biocompatible fluid and a proximal end of said hollow guidewire is inserted into said central bore, said stopper limits insertion of said proximal end of said hollow guidewire, thereby leaving an air bubble between the biocompatible fluid and said non-volatile fluid so as to avoid contact between said non-volatile liquid and the biocompatible fluid.

5. The pressure-measuring guidewire system of claim 4, wherein said hollow guidewire comprises an elongated flexible shaft having a terminal portion terminating at a distal tip, wherein said terminal portion comprises a helical spring surrounding a central channel, and wherein said distal tip is an open distal tip defining an opening aligned with said central channel, said inner lumen being contiguous with said central channel and extending to said open distal tip.

6. The system of claim 5, wherein said hollow guidewire has a length and an external diameter, said length being in excess of 1000 times said external diameter, and wherein said hollow guidewire is flexible and configured for use in a percutaneous coronary intervention.

7. The system of claim 5, wherein said open distal tip is formed by an end of said helical spring.

8. The system of claim 5, wherein a flexible coating circumscribes said helical spring along a majority of a length of said terminal portion.

9. The system of claim 5, wherein a length of said helical spring is at least about 10 centimeters.

10. The system of claim 5, wherein said internal volume is bordered by a septum, and wherein said pressure sensor has a hollow needle, the fluid connection between said internal volume and said sensing cavity of said pressure sensor being provided by penetration of said septum by said hollow needle.

11. The system of claim 5, further comprising:
   (a) a processing system comprising at least one processor, said processing system being electrically connected to said transducer so as to receive an output of said transducer;
   (b) a display associated with said processing system; and
   (c) a user input associated with said processing system,
wherein said processing system is responsive to said user input and configured to:
   (i) in response to a first user input, record a pressure corresponding to a pressure at a first position of a distal tip of the guidewire;
   (ii) in response to a second user input, record a pressure corresponding to a pressure at a second position of a distal tip of the guidewire; and
   (iii) display on said display at least one parameter indicative of a relationship between said pressures at said second position and at said first position.

12. The system of claim 11, wherein said pressure sensor, said processing system, said display and said user input are all provided carried by a single housing, said single housing being configured for selectively mating with said hollow guidewire.

* * * * *